US009693736B2

(12) United States Patent
Baker, Jr. et al.

(10) Patent No.: US 9,693,736 B2
(45) Date of Patent: Jul. 4, 2017

(54) SYSTEMS AND METHODS FOR DETERMINING RESPIRATION INFORMATION USING HISTORICAL DISTRIBUTION (75) Inventors: Clark R. Baker, Jr., Newman, CA (US); James Ochs, Seattle, WA (US); James H. Dripps, West Linton (GB); Paul S. Addison, Midlothian (GB)

(73) Assignee: Nellcor Puritan Bennett Ireland, Galway (IE)

( * ) Notice: Subject to any disclaimer, the term of this patent is extended or adjusted under 35 U.S.C. 154(b) by 1436 days.

(21) Appl. No.: 13/307,531

(22) Filed: Nov. 30, 2011

(65) Prior Publication Data
US 2013/0137936 A1 May 30, 2013

(51) Int. Cl.
A61B 5/08 (2006.01)
A61B 5/00 (2006.01)
A61B 5/1455 (2006.01)

(52) U.S. Cl.
CPC .......... *A61B 5/7246* (2013.01); *A61B 5/0816* (2013.01); *A61B 5/14552* (2013.01); *A61B 5/7278* (2013.01)

(58) Field of Classification Search
None
See application file for complete search history.

(56) References Cited

U.S. PATENT DOCUMENTS

| 5,188,108 A | 2/1993 | Secker |
| 5,243,993 A * | 9/1993 | Alexander ........... A61B 5/0245 600/517 |
| 5,279,296 A | 1/1994 | Thurston et al. |
| 5,285,783 A | 2/1994 | Secker |
| 5,285,784 A | 2/1994 | Seeker |
| 5,368,026 A | 11/1994 | Swedlow et al. |
| 5,368,041 A | 11/1994 | Shambroom |
| 5,398,682 A | 3/1995 | Lynn |
| 5,558,096 A * | 9/1996 | Palatnik ............ A61B 5/024 600/500 |
| 5,584,295 A | 12/1996 | Muller et al. |
| 5,588,425 A | 12/1996 | Sackner et al. |
| 5,605,151 A | 2/1997 | Lynn |

(Continued)

FOREIGN PATENT DOCUMENTS

| CN | 1430372 A | 7/2003 |
| EP | 0072601 A1 | 2/1983 |

(Continued)

OTHER PUBLICATIONS

Sukor et al., Signal quality measures for pulse oximetry through waveform morphology analysis, Physiol. Meas. 32, Feb. 2011, pp. 369-384).*

(Continued)

*Primary Examiner* — Michael Kahelin
*Assistant Examiner* — Tho Tran
(74) *Attorney, Agent, or Firm* — Shvarts & Leiz LLP (57) ABSTRACT A patient monitoring system may generate an autocorrelation sequence for a physiological signal such as a photoplethysmograph signal. A series of peak values may be identified for the autocorrelation sequence. The peak values may be modified based on a historical distribution of a physiological parameter. A physiological parameter such as respiration rate may be determined based on the modified peak values.

14 Claims, 6 Drawing Sheets

(56) References Cited

U.S. PATENT DOCUMENTS

| | | | |
|---|---|---|---|
| 5,738,104 A * | 4/1998 | Lo | A61B 5/02438 600/509 |
| 5,862,805 A | 1/1999 | Nitzan | |
| 5,865,736 A | 2/1999 | Baker et al. | |
| 5,891,023 A | 4/1999 | Lynn | |
| 6,002,952 A | 12/1999 | Diab et al. | |
| 6,035,223 A | 3/2000 | Baker | |
| 6,081,742 A | 6/2000 | Amano et al. | |
| 6,095,984 A | 8/2000 | Amano et al. | |
| 6,129,675 A | 10/2000 | Jay | |
| 6,135,966 A | 10/2000 | Ko | |
| 6,178,261 B1 | 1/2001 | Williams et al. | |
| 6,223,064 B1 | 4/2001 | Lynn | |
| 6,229,856 B1 | 5/2001 | Diab et al. | |
| 6,238,351 B1 | 5/2001 | Orr et al. | |
| 6,325,761 B1 | 12/2001 | Jay | |
| 6,334,065 B1 | 12/2001 | Al-Ali et al. | |
| 6,342,039 B1 | 1/2002 | Lynn et al. | |
| 6,347,006 B1 | 2/2002 | Parry et al. | |
| 6,350,242 B1 | 2/2002 | Doten et al. | |
| 6,405,076 B1 | 6/2002 | Taylor et al. | |
| 6,408,198 B1 | 6/2002 | Hanna et al. | |
| 6,434,408 B1 | 8/2002 | Heckel | |
| 6,463,311 B1 | 10/2002 | Diab | |
| 6,506,153 B1 | 1/2003 | Littek et al. | |
| 6,561,986 B2 | 5/2003 | Baura et al. | |
| 6,564,077 B2 | 5/2003 | Mortara | |
| 6,606,511 B1 | 8/2003 | Al-Ali et al. | |
| 6,609,016 B1 | 8/2003 | Lynn | |
| 6,684,090 B2 | 1/2004 | Al-Ali et al. | |
| 6,694,178 B1 | 2/2004 | Soula et al. | |
| 6,701,170 B2 | 3/2004 | Stetson | |
| 6,702,752 B2 | 3/2004 | Dekker | |
| 6,709,402 B2 | 3/2004 | Dekker | |
| 6,748,252 B2 | 6/2004 | Lynn et al. | |
| 6,754,516 B2 | 6/2004 | Mannheimer | |
| 6,760,608 B2 | 7/2004 | Lynn | |
| 6,783,498 B2 | 8/2004 | Sackner et al. | |
| 6,816,741 B2 | 11/2004 | Diab | |
| 6,839,581 B1 | 1/2005 | El-Solh et al. | |
| 6,839,582 B2 | 1/2005 | Heckel | |
| 6,896,661 B2 | 5/2005 | Dekker | |
| 6,905,470 B2 | 6/2005 | Lee et al. | |
| 6,925,324 B2 | 8/2005 | Shusterman | |
| 6,931,269 B2 | 8/2005 | Terry | |
| 6,966,878 B2 | 11/2005 | Schoisswohl et al. | |
| 6,970,792 B1 | 11/2005 | Diab | |
| 6,980,679 B2 | 12/2005 | Jeung et al. | |
| 6,990,426 B2 | 1/2006 | Yoon et al. | |
| 7,020,507 B2 | 3/2006 | Scharf et al. | |
| 7,025,728 B2 | 4/2006 | Ito et al. | |
| 7,035,679 B2 | 4/2006 | Addison et al. | |
| 7,043,293 B1 | 5/2006 | Baura | |
| 7,044,918 B2 | 5/2006 | Diab | |
| 7,070,566 B2 | 7/2006 | Medero et al. | |
| 7,079,880 B2 | 7/2006 | Stetson | |
| 7,079,888 B2 | 7/2006 | Oung et al. | |
| 7,147,601 B2 | 12/2006 | Marks et al. | |
| 7,177,682 B2 | 2/2007 | Lovett | |
| 7,190,261 B2 | 3/2007 | Al-Ali | |
| 7,215,986 B2 | 5/2007 | Diab et al. | |
| 7,218,966 B2 | 5/2007 | Haefner | |
| 7,254,425 B2 | 8/2007 | Lowery et al. | |
| 7,283,870 B2 | 10/2007 | Kaiser et al. | |
| 7,336,982 B2 | 2/2008 | Yoo | |
| 7,343,187 B2 | 3/2008 | Stetson | |
| 7,355,512 B1 | 4/2008 | Al-Ali | |
| 7,364,550 B1 | 4/2008 | Turcott | |
| 7,367,339 B2 | 5/2008 | Hickle | |
| 7,367,949 B2 | 5/2008 | Korhonen et al. | |
| 7,398,115 B2 | 7/2008 | Lynn | |
| 7,403,806 B2 | 7/2008 | Norris | |
| 7,407,486 B2 | 8/2008 | Huiku et al. | |
| 7,409,241 B2 | 8/2008 | Vitali et al. | |
| 7,415,297 B2 | 8/2008 | Al-Ali et al. | |
| 7,438,683 B2 | 10/2008 | Al-Ali et al. | |
| 7,440,787 B2 | 10/2008 | Diab | |
| 7,470,235 B2 | 12/2008 | Moriya et al. | |
| 7,485,095 B2 | 2/2009 | Shusterman | |
| 7,496,393 B2 | 2/2009 | Diab et al. | |
| 7,499,835 B2 | 3/2009 | Weber et al. | |
| 7,523,011 B2 | 4/2009 | Akiyama et al. | |
| 7,561,912 B2 | 7/2009 | Schatz et al. | |
| 7,610,324 B2 | 10/2009 | Troyansky et al. | |
| 7,690,378 B1 | 4/2010 | Turcott | |
| 7,785,262 B2 | 8/2010 | Melker et al. | |
| 7,801,591 B1 | 9/2010 | Shusterman | |
| 7,869,980 B2 | 1/2011 | Casler et al. | |
| 7,894,868 B2 | 2/2011 | Al-Ali et al. | |
| 7,899,507 B2 | 3/2011 | Al-Ali et al. | |
| 7,976,472 B2 | 7/2011 | Kiani | |
| 7,988,637 B2 | 8/2011 | Diab | |
| 8,019,400 B2 | 9/2011 | Diab et al. | |
| 8,046,040 B2 | 10/2011 | Ali et al. | |
| 8,130,105 B2 | 3/2012 | Al-Ali et al. | |
| 8,203,438 B2 | 6/2012 | Kiani et al. | |
| 8,275,553 B2 | 9/2012 | Amundson et al. | |
| 8,364,226 B2 | 1/2013 | Diab et al. | |
| 8,768,424 B2 | 7/2014 | Crowe et al. | |
| 2002/0117173 A1 | 8/2002 | Lynn et al. | |
| 2003/0036685 A1 | 2/2003 | Goodman | |
| 2003/0158466 A1 | 8/2003 | Lynn | |
| 2003/0163054 A1 | 8/2003 | Dekker | |
| 2003/0212336 A1 * | 11/2003 | Lee | A61B 5/02416 600/504 |
| 2003/0236647 A1 | 12/2003 | Yoon et al. | |
| 2004/0015091 A1 | 1/2004 | Greenwald et al. | |
| 2004/0260186 A1 | 12/2004 | Dekker | |
| 2005/0004479 A1 | 1/2005 | Townsend et al. | |
| 2005/0022606 A1 | 2/2005 | Partin et al. | |
| 2005/0027205 A1 | 2/2005 | Tarassenko et al. | |
| 2005/0049470 A1 | 3/2005 | Terry | |
| 2005/0070774 A1 | 3/2005 | Addison et al. | |
| 2005/0209517 A1 | 9/2005 | Diab et al. | |
| 2005/0222502 A1 | 10/2005 | Cooper | |
| 2005/0222503 A1 | 10/2005 | Dunlop et al. | |
| 2006/0122476 A1 | 6/2006 | Van Slyke | |
| 2006/0167366 A1 | 7/2006 | Tomita | |
| 2006/0192667 A1 | 8/2006 | Al-Ali | |
| 2006/0211930 A1 | 9/2006 | Scharf et al. | |
| 2006/0217614 A1 | 9/2006 | Takala et al. | |
| 2006/0258921 A1 | 11/2006 | Addison et al. | |
| 2006/0293574 A1 | 12/2006 | Norris | |
| 2007/0004977 A1 | 1/2007 | Norris | |
| 2007/0010723 A1 | 1/2007 | Uetela et al. | |
| 2007/0066914 A1 | 3/2007 | Le et al. | |
| 2007/0073120 A1 | 3/2007 | Li et al. | |
| 2007/0073124 A1 | 3/2007 | Li et al. | |
| 2007/0129636 A1 | 6/2007 | Friedman et al. | |
| 2007/0135722 A1 | 6/2007 | Lin | |
| 2007/0142719 A1 | 6/2007 | Kawasaki et al. | |
| 2007/0149890 A1 | 6/2007 | Li et al. | |
| 2007/0156193 A1 | 7/2007 | Cho et al. | |
| 2007/0179369 A1 | 8/2007 | Baker | |
| 2007/0213619 A1 | 9/2007 | Linder | |
| 2007/0213621 A1 | 9/2007 | Reisfeld et al. | |
| 2007/0225581 A1 | 9/2007 | Diab et al. | |
| 2007/0255146 A1 | 11/2007 | Andrews et al. | |
| 2007/0293896 A1 | 12/2007 | Haefner | |
| 2008/0077022 A1 | 3/2008 | Baker | |
| 2008/0081325 A1 | 4/2008 | Mannheimer et al. | |
| 2008/0167540 A1 | 7/2008 | Korhonen et al. | |
| 2008/0167541 A1 * | 7/2008 | Takala et al. | 600/323 |
| 2008/0200775 A1 | 8/2008 | Lynn | |
| 2009/0018409 A1 | 1/2009 | Banet et al. | |
| 2009/0171226 A1 * | 7/2009 | Campbell | A61B 5/02405 600/508 |
| 2009/0247837 A1 | 10/2009 | Ochs et al. | |
| 2009/0306487 A1 | 12/2009 | Crowe et al. | |
| 2009/0326349 A1 | 12/2009 | McGonigle | |
| 2009/0326351 A1 | 12/2009 | Addison et al. | |
| 2009/0326395 A1 | 12/2009 | Watson | |
| 2009/0326831 A1 | 12/2009 | McGonigle et al. | |
| 2010/0004552 A1 | 1/2010 | Zhang et al. | |

(56) References Cited

U.S. PATENT DOCUMENTS

| | | | |
|---|---|---|---|
| 2010/0016693 | A1 | 1/2010 | Addison et al. |
| 2010/0016696 | A1 | 1/2010 | Addison et al. |
| 2010/0113904 | A1 | 5/2010 | Batchelder et al. |
| 2010/0113908 | A1 | 5/2010 | Vargas et al. |
| 2010/0113909 | A1 | 5/2010 | Batchelder et al. |
| 2010/0249611 | A1 | 9/2010 | Chen et al. |
| 2010/0286495 | A1 | 11/2010 | McGonigle |
| 2010/0298676 | A1 | 11/2010 | Addison et al. |
| 2010/0298730 | A1 | 11/2010 | Tarassenko et al. |
| 2011/0066062 | A1 | 3/2011 | Banet et al. |
| 2011/0071406 | A1 | 3/2011 | Addison et al. |
| 2011/0245628 | A1 | 10/2011 | Baker, Jr. et al. |
| 2011/0251493 | A1 | 10/2011 | Poh et al. |
| 2011/0301427 | A1 | 12/2011 | Fu et al. |
| 2012/0136605 | A1 | 5/2012 | Addison et al. |
| 2013/0079606 | A1 | 3/2013 | McGonigle et al. |
| 2013/0296660 | A1 | 11/2013 | Tsien et al. |

FOREIGN PATENT DOCUMENTS

| | | | | |
|---|---|---|---|---|
| EP | 1344488 | A2 | 9/2004 | |
| EP | 1507474 | B1 | 2/2009 | |
| WO | WO 92/15955 | | 9/1992 | |
| WO | WO00/21438 | * | 10/1999 | ............... A61B 5/00 |
| WO | WO 00/21438 | | 4/2000 | |
| WO | WO 03/000125 | A1 | 1/2003 | |
| WO | WO 03/055395 | A1 | 7/2003 | |
| WO | WO 03/084396 | A1 | 10/2003 | |
| WO | WO 04/075746 | A2 | 9/2004 | |
| WO | WO 2005/064314 | | 7/2005 | |
| WO | WO 2010/030238 | A1 | 3/2010 | |

OTHER PUBLICATIONS

Stagg and Gennser, "Electronic analysis of foetal breathing movements: A practical application of phase-locked-loop principles," Journal of Med. Eng. and Tech., Sep. 1978, vol. 2, No. 5, pp. 246-249.

Rapaport and Cousin, "New phase-lock tracking instrument for foetal breathing monitoring," Med. & Biol. Eng. & Comp. 1982, vol. 20, pp. 1-6.

Lindberg, L.G., Ughall, H., Oberg, P.A., "Monitoring of respiratory and heart rates using a fibre-optic sensor," Medical & Biological Engineering & Computing, Sep. 1992, pp. 533-537.

International Search Report and Written Opinion of the International Searching Authority for application No. PCT/US2012/066197, mailed on Feb. 28, 2013.

The FastICA Algorithm for Independent Component Analysis and Projection Pursuit, (Dec. 21, 2010).

Aapo Hyvarinen & Erkki Oja, Independent Component Analysis: Algorithms and Applications, Neural Networks 13(4-5): 411-430, (2000).

Li et al. "Comparison of respiratory-induced variations in photoplethysmographic signals." Physiol Meas. Mar. 2010;31 (3):415-25. Epub Feb. 10, 2010.

Madhav et al. "Estimation of respiratory rate from principal components of photoplethysmographic signals." 2010 IEEE EMBS Conference on Biomedical Engineering and Sciences (IECBES), pp. 311-314. Nov. 30, 2010-Dec. 2, 2010.

Madhav et al. "Extraction of Respiratory Activity from PPG and BP signals using Principal Component Analysis." 2011 International Conference on Communications and Signal Processing (ICCSP), pp. 452-456. Feb. 10-12, 2011.

Langley et al. "Principal Component Analysis as a Tool for Analyzing Beat-to-Beat Changes in ECG Features: Application ECG-Derived Respiration." EEE Trans Biomed Eng. Apr. 2010;57(4):821-9. Epub Apr. 7, 2009.

International Search Report and Written Opinion of the International Searching Authority for Application No. PCT/EP2012/068559, mailed on Jan. 16, 2013, 11 pages.

International Search Report and Written Opinion of the International Searching Authority for Application No. PCT/US2012/056636, mailed on Jan. 23, 2013, 12 pages.

International Search Report and Written Opinion of the International Searching Authority for Application No. PCT/US2013/020331, mailed on Apr. 4, 2013.

* cited by examiner

SYSTEMS AND METHODS FOR DETERMINING RESPIRATION INFORMATION USING HISTORICAL DISTRIBUTION

The present disclosure relates to physiological signal processing, and more particularly relates to determining a physiological parameter such as respiration information from a physiological signal based on a historical distribution.

SUMMARY

A patient monitoring system may receive a physiological signal such as a photoplethysmograph signal. A plurality of morphology metric signals may be generated from the PPG signal, an autocorrelation sequence may be generated for each morphology metric signal, and the autocorrelation sequences may be combined. A physiological parameter such as respiration information may be determined based on the resulting autocorrelation sequence.

In some instances other physiological phenomena other than the targeted physiological parameter may have an impact on the physiological signal such that the autocorrelation sequence does not yield an accurate result for the physiological parameter. A historical distribution of the physiological parameter may be used to modify the values of the autocorrelation sequence. The physiological parameter may be determined based on the modified autocorrelation sequence.

BRIEF DESCRIPTION OF THE FIGURES

The above and other features of the present disclosure, its nature and various advantages will be more apparent upon consideration of the following detailed description, taken in conjunction with the accompanying drawings in which.

DETAILED DESCRIPTION OF THE FIGURES

A patient monitoring system may receive a physiological signal such as a photoplethysmograph (PPG) signal. In addition to including information about pulse waves, the PPG signal may exhibit long term and short term modulations that may be used to determine other physiological parameters such as respiration rate. A plurality of morphology metric signals may be generated from the PPG signal to identify modulations that are related to respiration. An autocorrelation sequence may be generated for each morphology metric signal and the autocorrelation sequences may be combined. The peaks of the combined autocorrelation sequence may be used to identify periodic components of the morphology metric signals. These periodic components may be used to determine the respiration rate.

In some instances the autocorrelation sequence may have peaks that correspond to periodic phenomena other than respiration, such as vasomotion or certain arrhythmias. A historical distribution of respiration rate values may be used to distinguish respiration from other periodic phenomena, based in part on the observation that respiration generally changes slowly over time. The current autocorrelation sequence may be weighted based on the historical distribution, resulting in additional emphasis on autocorrelation peaks that track the historical distribution. The respiration rate may be determined based on the historical distribution.

For purposes of clarity, the present disclosure is written in the context of the physiological signal being a PPG signal generated by a pulse oximetry system. It will be understood that any other suitable physiological signal or any other suitable system may be used in accordance with the teachings of the present disclosure.

An oximeter is a medical device that may determine the oxygen saturation of the blood. One common type of oximeter is a pulse oximeter, which may indirectly measure the oxygen saturation of a patient's blood (as opposed to measuring oxygen saturation directly by analyzing a blood sample taken from the patient). Pulse oximeters may be included in patient monitoring systems that measure and display various blood flow characteristics including, but not limited to, the oxygen saturation of hemoglobin in arterial blood. Such patient monitoring systems may also measure and display additional physiological parameters, such as a patient's pulse rate.

An oximeter may include a light sensor that is placed at a site on a patient, typically a fingertip, toe, forehead or earlobe, or in the case of a neonate, across a foot. The oximeter may use a light source to pass light through blood perfused tissue and photoelectrically sense the absorption of the light in the tissue. In addition, locations that are not typically understood to be optimal for pulse oximetry serve as suitable sensor locations for the monitoring processes described herein, including any location on the body that has a strong pulsatile arterial flow. For example, additional suitable sensor locations include, without limitation, the neck to monitor carotid artery pulsatile flow, the wrist to monitor radial artery pulsatile flow, the inside of a patient's thigh to monitor femoral artery pulsatile flow, the ankle to monitor tibial artery pulsatile flow, and around or in front of the ear. Suitable sensors for these locations may include sensors for sensing absorbed light based on detecting reflected light. In all suitable locations, for example, the oximeter may measure the intensity of light that is received at the light sensor as a function of time. The oximeter may also include sensors at multiple locations. A signal representing light intensity versus time or a mathematical manipulation of this signal (e.g., a scaled version thereof, a log taken thereof, a scaled version of a log taken thereof, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. The light intensity or the amount of light absorbed may then be used to calculate any of a number of physiological parameters, including an amount of a blood constituent (e.g., oxyhemoglobin) being measured as well as a pulse rate and when each individual pulse occurs.

In some applications, the light passed through the tissue is selected to be of one or more wavelengths that are absorbed by the blood in an amount representative of the amount of the blood constituent present in the blood. The amount of light passed through the tissue varies in accordance with the changing amount of blood constituent in the tissue and the related light absorption. Red and infrared (IR) wavelengths may be used because it has been observed that highly oxygenated blood will absorb relatively less Red light and more IR light than blood with a lower oxygen saturation. By comparing the intensities of two wavelengths at different points in the pulse cycle, it is possible to estimate the blood oxygen saturation of hemoglobin in arterial blood.

When the measured blood parameter is the oxygen saturation of hemoglobin, a convenient starting point assumes a saturation calculation based at least in part on Lambert-Beer's law. The following notation will be used herein:

$$I(\lambda,t)=I_O(\lambda)\exp(-(s\beta_O(\lambda)+(1-s)\beta_r(\lambda))l(t)) \quad (1)$$

where:
$\lambda$=wavelength;
t=time;
I=intensity of light detected;
$I_0$=intensity of light transmitted;
s=oxygen saturation;
$\beta_o$, $\beta_r$=empirically derived absorption coefficients; and
l(t)=a combination of concentration and path length from emitter to detector as a function of time.

The traditional approach measures light absorption at two wavelengths (e.g., Red and IR), and then calculates saturation by solving for the "ratio of ratios" as follows.

1. The natural logarithm of Eq. 1 is taken ("log" will be used to represent the natural logarithm) for IR and Red to yield $$\log I = \log I_O - (s\beta_O + (1-s)\beta_r)l. \quad (2)$$

2. Eq. 2 is then differentiated with respect to time to yield $$\frac{d\log I}{dt} = -(s\beta_o + (1-s)\beta_r)\frac{dl}{dt}. \quad (3)$$

3. Eq. 3, evaluated at the Red wavelength $\lambda_R$, is divided by Eq. 3 evaluated at the IR wavelength $\lambda_{IR}$ in accordance with $$\frac{d\log I(\lambda_R)/dt}{d\log I(\lambda_{IR})/dt} = \frac{s\beta_o(\lambda_R)+(1-s)\beta_r(\lambda_R)}{s\beta_o(\lambda_{IR})+(1-s)\beta_r(\lambda_{IR})}. \quad (4)$$

4. Solving for s yields $$s = \frac{\frac{d\log I(\lambda_{IR})}{dt}\beta_r(\lambda_R) - \frac{d\log I(\lambda_R)}{dt}\beta_r(\lambda_{IR})}{\frac{d\log I(\lambda_R)}{dt}(\beta_o(\lambda_{IR})-\beta_r(\lambda_{IR})) - \frac{d\log I(\lambda_{IR})}{dt}(\beta_o(\lambda_R)-\beta_r(\lambda_R))}. \quad (5)$$

5. Note that, in discrete time, the following approximation can be made:

$$\frac{d\log I(\lambda,t)}{dt} \simeq \log I(\lambda,t_2) - \log I(\lambda,t_1). \quad (6)$$

6. Rewriting Eq. 6 by observing that log A−log B=log(A/B) yields $$\frac{d\log I(\lambda,t)}{dt} \simeq \log\left(\frac{I(t_2,\lambda)}{I(t_1,\lambda)}\right). \quad (7)$$

7. Thus, Eq. 4 can be expressed as $$\frac{\frac{d\log I(\lambda_R)}{dt}}{\frac{d\log I(\lambda_{IR})}{dt}} \simeq \frac{\log\left(\frac{I(t_1,\lambda_R)}{I(t_2,\lambda_R)}\right)}{\log\left(\frac{I(t_1,\lambda_{IR})}{I(t_2,\lambda_{IR})}\right)} = R, \quad (8)$$

where R represents the "ratio of ratios."

8. Solving Eq. 4 for s using the relationship of Eq. 5 yields $$s = \frac{\beta_r(\lambda_R) - R\beta_r(\lambda_{IR})}{R(\beta_o(\lambda_{IR})-\beta_r(\lambda_{IR})) - (\beta_o(\lambda_R)-\beta_r(\lambda_R))}. \quad (9)$$

9. From Eq. 8, R can be calculated using two points (e.g., PPG maximum and minimum), or a family of points. One method applies a family of points to a modified version of Eq. 8. Using the relationship $$\frac{d\log I}{dt} = \frac{dI/dt}{I}, \quad (10)$$

Eq. 8 becomes $$\frac{\frac{d\log I(\lambda_R)}{dt}}{\frac{d\log I(\lambda_{IR})}{dt}} \simeq \frac{\frac{I(t_2,\lambda_R)-I(t_1,\lambda_R)}{I(t_1,\lambda_R)}}{\frac{I(t_2,\lambda_{IR})-I(t_1,\lambda_{IR})}{I(t_1,\lambda_{IR})}} \quad (11)$$
$$= \frac{[I(t_2,\lambda_R)-I(t_1,\lambda_R)]I(t_1,\lambda_{IR})}{[I(t_2,\lambda_{IR})-I(t_1,\lambda_{IR})]I(t_1,\lambda_R)}$$
$$= R,$$

which defines a cluster of points whose slope of y versus x will give R when $$x=[I(t_2,\lambda_{IR})-I(t_1,\lambda_{IR})]I(t_1,\lambda_R), \quad (12)$$

and $$y=[I(t_2,\lambda_R)-I(t_1,\lambda_R)]I(t_1,\lambda_{IR}). \quad (13)$$

Once R is determined or estimated, for example, using the techniques described above, the blood oxygen saturation can be determined or estimated using any suitable technique for relating a blood oxygen saturation value to R. For example, blood oxygen saturation can be determined from empirical data that may be indexed by values of R, and/or it may be determined from curve fitting and/or other interpolative techniques.

Figure 1:
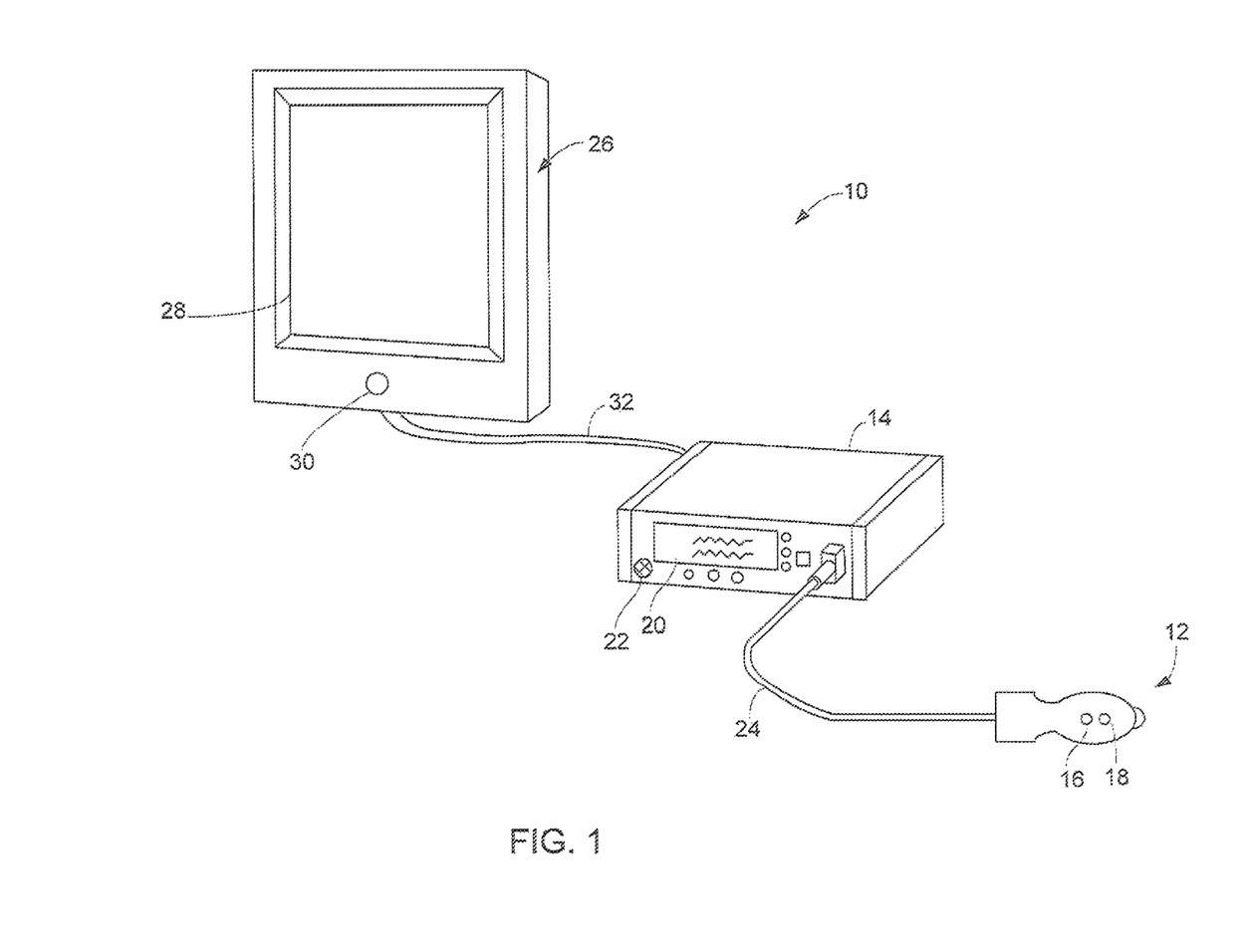
FIG. 1 shows an illustrative patient monitoring system in accordance with some embodiments of the present disclosure.

FIG. 1 is a perspective view of an embodiment of a patient monitoring system 10. System 10 may include sensor unit 12 and monitor 14. In some embodiments, sensor unit 12 may be part of an oximeter. Sensor unit 12 may include an emitter 16 for emitting light at one or more wavelengths into a patient's tissue. A detector 18 may also be provided in sensor unit 12 for detecting the light originally from emitter 16 that emanates from the patient's tissue after passing through the tissue. Any suitable physical configuration of emitter 16 and detector 18 may be used. In an embodiment, sensor unit 12 may include multiple emitters and/or detectors, which may be spaced apart. System 10 may also include one or more additional sensor units (not shown) that may take the form of any of the embodiments described herein with reference to sensor unit 12. An additional sensor unit may be the same type of sensor unit as sensor unit 12, or a different sensor unit type than sensor unit 12. Multiple sensor units may be capable of being positioned at two different locations on a subject's body; for example, a first sensor unit may be positioned on a patient's forehead, while a second sensor unit may be positioned at a patient's fingertip.

Sensor units may each detect any signal that carries information about a patient's physiological state, such as an electrocardiograph signal, arterial line measurements, or the pulsatile force exerted on the walls of an artery using, for example, oscillometric methods with a piezoelectric transducer. According to another embodiment, system 10 may include two or more sensors forming a sensor array in lieu of either or both of the sensor units. Each of the sensors of a sensor array may be a complementary metal oxide semiconductor (CMOS) sensor. Alternatively, each sensor of an array may be charged coupled device (CCD) sensor. In some embodiments, a sensor array may be made up of a combination of CMOS and CCD sensors. The CCD sensor may comprise a photoactive region and a transmission region for receiving and transmitting data whereas the CMOS sensor may be made up of an integrated circuit having an array of pixel sensors. Each pixel may have a photodetector and an active amplifier. It will be understood that any type of sensor, including any type of physiological sensor, may be used in one or more sensor units in accordance with the systems and techniques disclosed herein. It is understood that any number of sensors measuring any number of physiological signals may be used to determine physiological information in accordance with the techniques described herein.

In some embodiments, emitter 16 and detector 18 may be on opposite sides of a digit such as a finger or toe, in which case the light that is emanating from the tissue has passed completely through the digit. In some embodiments, emitter 16 and detector 18 may be arranged so that light from emitter 16 penetrates the tissue and is reflected by the tissue into detector 18, such as in a sensor designed to obtain pulse oximetry data from a patient's forehead.

In some embodiments, sensor unit 12 may be connected to and draw its power from monitor 14 as shown. In another embodiment, the sensor may be wirelessly connected to monitor 14 and include its own battery or similar power supply (not shown). Monitor 14 may be configured to calculate physiological parameters (e.g., pulse rate, blood oxygen saturation, and respiration information) based at least in part on data relating to light emission and detection received from one or more sensor units such as sensor unit 12 and an additional sensor (not shown). In some embodiments, the calculations may be performed on the sensor units or an intermediate device and the result of the calculations may be passed to monitor 14. Further, monitor 14 may include a display 20 configured to display the physiological parameters or other information about the system. In the embodiment shown, monitor 14 may also include a speaker 22 to provide an audible sound that may be used in various other embodiments, such as for example, sounding an audible alarm in the event that a patient's physiological parameters are not within a predefined normal range. In some embodiments, the system 10 includes a stand-alone monitor in communication with the monitor 14 via a cable or a wireless network link.

In some embodiments, sensor unit 12 may be communicatively coupled to monitor 14 via a cable 24. In some embodiments, a wireless transmission device (not shown) or the like may be used instead of or in addition to cable 24. Monitor 14 may include a sensor interface configured to receive physiological signals from sensor unit 12, provide signals and power to sensor unit 12, or otherwise communicate with sensor unit 12. The sensor interface may include any suitable hardware, software, or both, which may be allow communication between monitor 14 and sensor unit 12.

Patient monitoring system 10 may also include display monitor 26. Monitor 14 may be in communication with display monitor 26. Display monitor 26 may be any electronic device that is capable of communicating with monitor 14 and calculating and/or displaying physiological parameters, e.g., a general purpose computer, tablet computer, smart phone, or an application-specific device. Display monitor 26 may include a display 28 and user interface 30. Display 28 may include touch screen functionality to allow a user to interface with display monitor 26 by touching display 28 and utilizing motions. User interface 30 may be any interface that allows a user to interact with display monitor 26, e.g., a keyboard, one or more buttons, a camera, or a touchpad.

Monitor 14 and display monitor 26 may communicate utilizing any suitable transmission medium, including wireless (e.g., WiFi, Bluetooth, etc.), wired (e.g., USB, Ethernet, etc.), or application-specific connections. In an exemplary embodiment, monitor 14 and display monitor 26 may be connected via cable 32. Monitor 14 and display monitor 26 may communicate utilizing standard or proprietary communications protocols, such as the Standard Host Interface Protocol (SHIP) developed and used by Covidien of Mansfield, Mass. In addition, monitor 14, display monitor 26, or both may be coupled to a network to enable the sharing of information with servers or other workstations (not shown). Monitor 14, display monitor 26, or both may be powered by a battery (not shown) or by a conventional power source such as a wall outlet.

Monitor 14 may transmit calculated physiological parameters (e.g., pulse rate, blood oxygen saturation, and respiration information) to display monitor 26. In some embodiments, monitor 14 may transmit a PPG signal, data representing a PPG signal, or both to display monitor 26, such that some or all calculated physiological parameters (e.g., pulse rate, blood oxygen saturation, and respiration information) may be calculated at display monitor 26. In an exemplary embodiment, monitor 14 may calculate pulse rate and blood oxygen saturation, while display monitor 26 may calculate respiration information such as a respiration rate.

Figure 2:
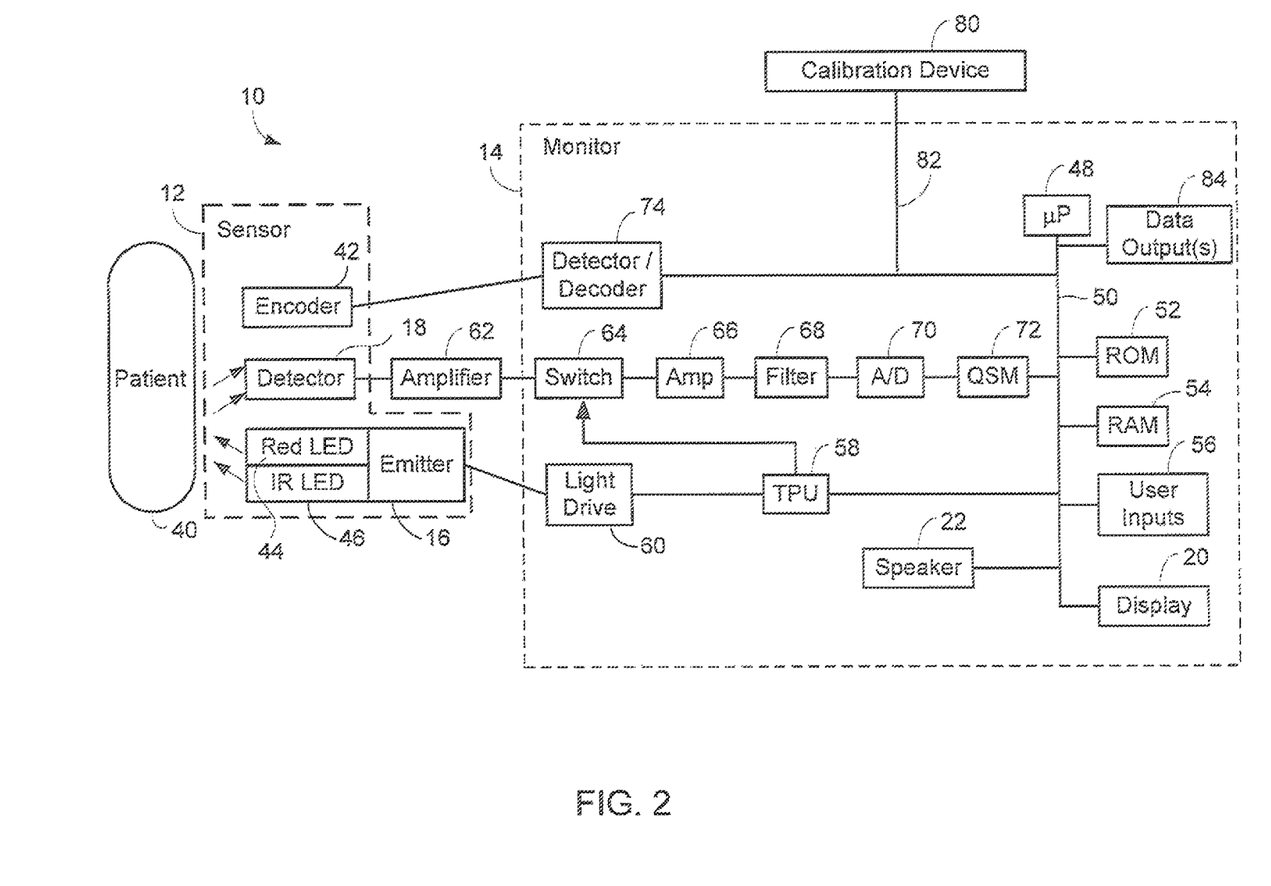
FIG. 2 is a block diagram of the illustrative patient monitoring system of FIG. 1 coupled to a patient in accordance with some embodiments of the present disclosure.

FIG. 2 is a block diagram of a patient monitoring system, such as patient monitoring system 10 of FIG. 1, which may be coupled to a patient 40 in accordance with an embodiment. Certain illustrative components of sensor unit 12 and monitor 14 are illustrated in FIG. 2.

Sensor unit 12 may include emitter 16, detector 18, and encoder 42. In the embodiment shown, emitter 16 may be configured to emit at least two wavelengths of light (e.g., Red and IR) into a patient's tissue 40. Hence, emitter 16 may include a Red light emitting light source such as Red light emitting diode (LED) 44 and an IR light emitting light source such as IR LED 46 for emitting light into the patient's tissue 40 at the wavelengths used to calculate the patient's physiological parameters. In some embodiments, the Red wavelength may be between about 600 nm and about 700 nm, and the IR wavelength may be between about 800 nm and about 1000 nm. In embodiments where a sensor array is used in place of a single sensor, each sensor may be configured to emit a single wavelength. For example, a first sensor may emit only a Red light while a second sensor may emit only an IR light. In a further example, the wavelengths of light used may be selected based on the specific location of the sensor.

It will be understood that, as used herein, the term "light" may refer to energy produced by radiation sources and may include one or more of radio, microwave, millimeter wave, infrared, visible, ultraviolet, gamma ray or X-ray electromagnetic radiation. As used herein, light may also include electromagnetic radiation having any wavelength within the radio, microwave, infrared, visible, ultraviolet, or X-ray spectra, and that any suitable wavelength of electromagnetic radiation may be appropriate for use with the present techniques. Detector 18 may be chosen to be specifically sensitive to the chosen targeted energy spectrum of the emitter 16.

In some embodiments, detector 18 may be configured to detect the intensity of light at the Red and IR wavelengths. Alternatively, each sensor in the array may be configured to detect an intensity of a single wavelength. In operation, light may enter detector 18 after passing through the patient's tissue 40. Detector 18 may convert the intensity of the received light into an electrical signal. The light intensity is directly related to the absorbance and/or reflectance of light in the tissue 40. That is, when more light at a certain wavelength is absorbed or reflected, less light of that wavelength is received from the tissue by the detector 18. After converting the received light to an electrical signal, detector 18 may send the signal to monitor 14, where physiological parameters may be calculated based on the absorption of the Red and IR wavelengths in the patient's tissue 40.

In some embodiments, encoder 42 may contain information about sensor unit 12, such as what type of sensor it is (e.g., whether the sensor is intended for placement on a forehead or digit) and the wavelengths of light emitted by emitter 16. This information may be used by monitor 14 to select appropriate algorithms, lookup tables and/or calibration coefficients stored in monitor 14 for calculating the patient's physiological parameters.

Encoder 42 may contain information specific to patient 40, such as, for example, the patient's age, weight, and diagnosis. This information about a patient's characteristics may allow monitor 14 to determine, for example, patient-specific threshold ranges in which the patient's physiological parameter measurements should fall and to enable or disable additional physiological parameter algorithms. This information may also be used to select and provide coefficients for equations from which measurements may be determined based at least in part on the signal or signals received at sensor unit 12. For example, some pulse oximetry sensors rely on equations to relate an area under a portion of a PPG signal corresponding to a physiological pulse to determine blood pressure. These equations may contain coefficients that depend upon a patient's physiological characteristics as stored in encoder 42. Encoder 42 may, for instance, be a coded resistor that stores values corresponding to the type of sensor unit 12 or the type of each sensor in the sensor array, the wavelengths of light emitted by emitter 16 on each sensor of the sensor array, and/or the patient's characteristics. In some embodiments, encoder 42 may include a memory on which one or more of the following information may be stored for communication to monitor 14; the type of the sensor unit 12; the wavelengths of light emitted by emitter 16; the particular wavelength each sensor in the sensor array is monitoring; a signal threshold for each sensor in the sensor array; any other suitable information; or any combination thereof.

In some embodiments, signals from detector 18 and encoder 42 may be transmitted to monitor 14. In the embodiment shown, monitor 14 may include a general-purpose microprocessor 48 connected to an internal bus 50. Microprocessor 48 may be adapted to execute software, which may include an operating system and one or more applications, as part of performing the functions described herein. Also connected to bus 50 may be a read-only memory (ROM) 52, a random access memory (RAM) 54, user inputs 56, display 20, data output 84, and speaker 22.

RAM 54 and ROM 52 are illustrated by way of example, and not limitation. Any suitable computer-readable media may be used in the system for data storage. Computer-readable media are capable of storing information that can be interpreted by microprocessor 48. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium that can be used to store the desired information and that can be accessed by components of the system.

In the embodiment shown, a time processing unit (TPU) 58 may provide timing control signals to light drive circuitry 60, which may control when emitter 16 is illuminated and multiplexed timing for Red LED 44 and IR LED 46. TPU 58 may also control the gating-in of signals from detector 18 through amplifier 62 and switching circuit 64. These signals are sampled at the proper time, depending upon which light source is illuminated. The received signal from detector 18 may be passed through amplifier 66, low pass filter 68, and analog-to-digital converter 70. The digital data may then be stored in a queued serial module (QSM) 72 (or buffer) for later downloading to RAM 54 as QSM 72 is filled. In some embodiments, there may be multiple separate parallel paths having components equivalent to amplifier 66, filter 68, and/or A/D converter 70 for multiple light wavelengths or spectra received. Any suitable combination of components (e.g., microprocessor 48, RAM 54, analog to digital converter 70, any other suitable component shown or not shown in FIG. 2) coupled by bus 50 or otherwise coupled (e.g., via an external bus), may be referred to as "processing equipment."

In some embodiments, microprocessor 48 may determine the patient's physiological parameters, such as $SpO_2$, pulse rate, and/or respiration information, using various algorithms and/or look-up tables based on the value of the received signals and/or data corresponding to the light received by detector 18. Signals corresponding to information about patient 40, and particularly about the intensity of light emanating from a patient's tissue over time, may be transmitted from encoder 42 to decoder 74. These signals may include, for example, encoded information relating to patient characteristics. Decoder 74 may translate these signals to enable the microprocessor to determine the thresholds based at least in part on algorithms or look-up tables stored in ROM 52. In some embodiments, user inputs 56 may be used to enter information, select one or more options, provide a response, input settings, any other suitable inputting function, or any combination thereof. User inputs 56 may be used to enter information about the patient, such as age, weight, height, diagnosis, medications, treatments, and so forth. In some embodiments, display 20 may exhibit a list of values, which may generally apply to the patient, such as, for example, age ranges or medication families, which the user may select using user inputs 56.

Calibration device 80, which may be powered by monitor 14 via a communicative coupling 82, a battery, or by a conventional power source such as a wall outlet, may include any suitable signal calibration device. Calibration device 80 may be communicatively coupled to monitor 14 via communicative coupling 82, and/or may communicate wirelessly (not shown). In some embodiments, calibration device 80 is completely integrated within monitor 14. In some embodiments, calibration device 80 may include a manual input device (not shown) used by an operator to manually input reference signal measurements obtained from some other source (e.g., an external invasive or non-invasive physiological measurement system).

Data output 84 may provide for communications with other devices such as display monitor 26 utilizing any suitable transmission medium, including wireless (e.g., WiFi, Bluetooth, etc.), wired (e.g., USB, Ethernet, etc.), or application-specific connections. Data output 84 may receive messages to be transmitted from microprocessor 48 via bus 50. Exemplary messages to be sent in an embodiment described herein may include PPG signals to be transmitted to display monitor module 26.

The optical signal attenuated by the tissue of patient 40 can be degraded by noise, among other sources. One source of noise is ambient light that reaches the light detector. Another source of noise is electromagnetic coupling from other electronic instruments. Movement of the patient also introduces noise and affects the signal. For example, the contact between the detector and the skin, or the emitter and the skin, can be temporarily disrupted when movement causes either to move away from the skin. Also, because blood is a fluid, it responds differently than the surrounding tissue to inertial effects, which may result in momentary changes in volume at the point to which the oximeter probe is attached.

Noise (e.g., from patient movement) can degrade a sensor signal relied upon by a care provider, without the care provider's awareness. This is especially true if the monitoring of the patient is remote, the motion is too small to be observed, or the care provider is watching the instrument or other parts of the patient, and not the sensor site. Processing sensor signals (e.g., PPG signals) may involve operations that reduce the amount of noise present in the signals, control the amount of noise present in the signal, or otherwise identify noise components in order to prevent them from affecting measurements of physiological parameters derived from the sensor signals.

Figure 3:
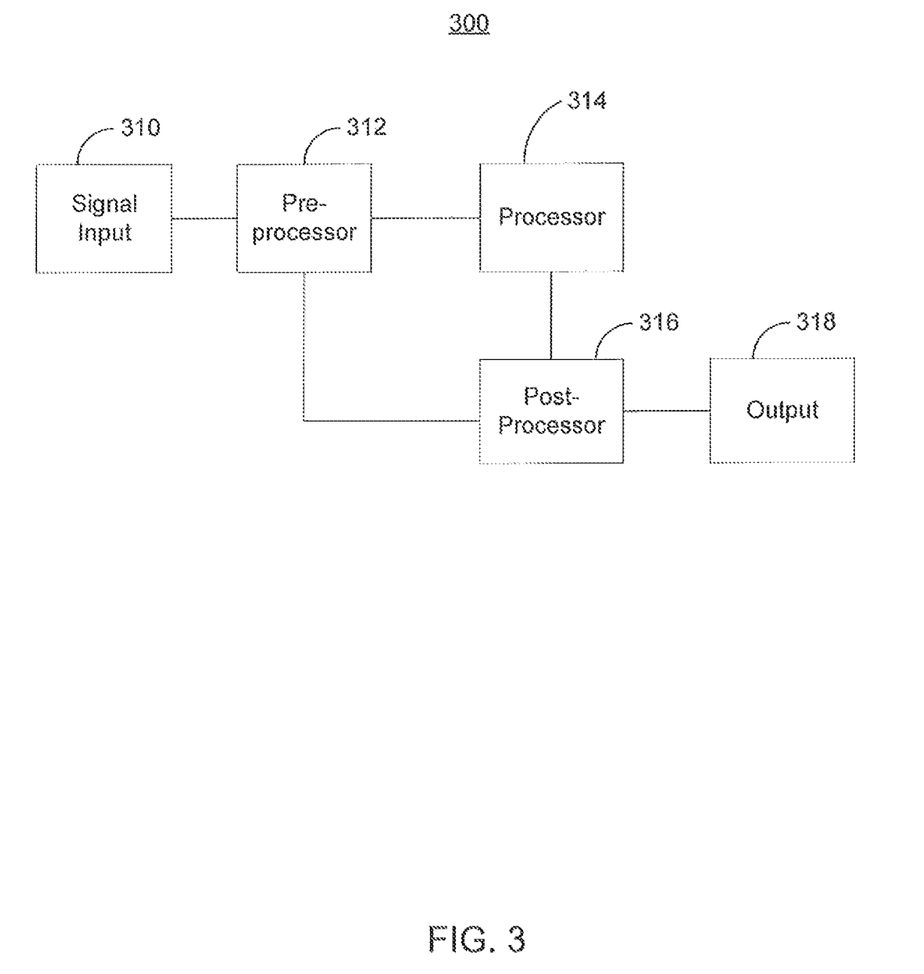
FIG. 3 shows a block diagram of an illustrative signal processing system in accordance with some embodiments of the present disclosure.

FIG. 3 is an illustrative processing system 300 in accordance with an embodiment that may implement the signal processing techniques described herein. In some embodiments, processing system 300 may be included in a patient monitoring system (e.g., patient monitoring system 10 of FIGS. 1-2). Processing system 300 may include input signal 310, pre-processor 312, processor 314, post-processor 316, and output 318. Pre-processor 312, processor 314, and post-processor 316 may be any suitable software, firmware, hardware, or combination thereof for calculating physiological parameters such as respiration information based on input signal 310. For example, pre-processor 312, processor 314, and post-processor 316 may include one or more hardware processors (e.g., integrated circuits), one or more software modules, computer-readable media such as memory, firmware, or any combination thereof. Pre-processor 312, processor 314, and post-processor 316 may, for example, be a computer or may be one or more chips (i.e., integrated circuits). Pre-processor 312, processor 314, and post-processor 316 may, for example, include an assembly of analog electronic components.

In some embodiments, processing system 300 may be included in monitor 14 and/or display monitor 26 of a patient monitoring system (e.g., patient monitoring system 10 of FIGS. 1-2). In the illustrated embodiment, input signal 310 may be a PPG signal. Input signal 310 may be a PPG signal that was sampled and generated at monitor 14, for example at 76 Hz. Input signal 310, pre-processor 312, processor 314, and post-processor 316 may reside entirely within a single device (e.g., monitor 14 or display monitor 26) or may reside in multiple devices (e.g., monitor 14 and display monitor 26).

Input signal 310 may be coupled to pre-processor 312. In some embodiments, input signal 310 may include PPG signals corresponding to one or more light frequencies, such as a Red PPG signal and an IR PPG signal. In some embodiments, the signal may include signals measured at one or more sites on a patient's body, for example, a patient's finger, toe, ear, arm, or any other body site. In some embodiments, signal 310 may include multiple types of signals (e.g., one or more of an ECG signal, an EEG signal, an acoustic signal, an optical signal, a signal representing a blood pressure, and a signal representing a heart rate). The signal may be any suitable biosignal or signals, such as, for example, electrocardiogram, electroencephalogram, electrogastrogram, electromyogram, heart rate signals, pathological sounds, ultrasound, or any other suitable biosignal. The systems and techniques described herein are also applicable to any dynamic signals, non-destructive testing signals, condition monitoring signals, fluid signals, geophysical signals, astronomical signals, electrical signals, financial signals including financial indices, sound and speech signals, chemical signals, meteorological signals including climate signals, any other suitable signal, and/or any combination thereof.

Pre-processor 312 may be implemented by any suitable combination of hardware and software. In an embodiment, pre-processor 312 may be any suitable signal processing device and the signal received from input signal 310 may include one or more PPG signals. An exemplary received PPG signal may be received in a streaming fashion, or may be received on a periodic basis as a sampling window, e.g., every 5 seconds. The received signal may include the PPG signal as well as other information related to the PPG signal, e.g., a pulse found indicator, the mean pulse rate from the PPG signal, the most recent pulse rate, an indicator for the most recent invalid sample, and an indicator of the last artifact for the PPG signal. It will be understood that input signal 310 may include any suitable signal source, signal generating data, signal generating equipment, or any combination thereof to be provided to pre-processor 312. The signal received at input signal 310 may be a single signal, or may be multiple signals transmitted over a single pathway or multiple pathways.

Pre-processor 312 may apply one or more signal processing operations to input signal 310. For example, pre-processor 312 may apply a pre-determined set of processing operations to input signal 310 to produce a signal that may be appropriately analyzed and interpreted by processor 314, post-processor 316, or both. Pre-processor 312 may perform any necessary operations to provide a signal that may be used as an input for processor 314 and post-processor 316 to determine physiological information such as respiration information. Examples include reshaping the signal for transmission, multiplexing the signal, modulating the signal onto carrier signals, compressing the signal, encoding the signal, filtering the signal, low-pass filtering, band-pass filtering, signal interpolation, downsampling of a signal, attenuating the signal, adaptive filtering, closed-loop filtering, any other suitable filtering, and/or any combination thereof.

Other signal processing operations may be performed by pre-processor 312 for each pulse and may be related to producing morphology metrics suitable as inputs to determine physiological information. Pre-processor 312 may perform calculations based on an analysis window of a series of recently received PPG signal sampling windows, e.g., a 45-second analysis window may correspond to the 9 most recent 5-second sampling windows. The physiological information may be respiration information, which may include any information relating to respiration, e.g., respiration rate, change in respiration rate, breathing intensity, etc. Because respiration has an impact on pulse characteristics, it may be possible to determine respiration information from a PPG signal. Morphology metrics may be parameters that may be calculated from the PPG signal that provide information related to respiration. Examples include a down metric for a pulse, kurtosis for a pulse, the delta of the second derivative between consecutive pulses, the up metric for a pulse, skew, b/a ratio, c/a ratio, peak amplitude of a pulse, center of gravity of a pulse, or area of a pulse, as described in more detail herein. Other information that may be determined by pre-processor 312 may include the pulse rate, the variability of the period of the PPG signal, the variability of the amplitude of the PPG signal, and an age measurement indicative of the age of the useful portion of the analyzed PPG signal.

In some embodiments, pre-processor 312 may be coupled to processor 314 and post-processor 316. Processor 314 and post-processor 316 may be implemented by any suitable combination of hardware and software. Processor 314 may receive physiological information and calculated parameters from pre-processor 312. For example, processor may receive morphology metrics for use in calculating morphology metric signals that may be used to determine respiration information, as well as pulse rate and an age for the morphology metric signals. For example, processor 314 may receive samples representing a number of morphology metric values, such as down metric calculations, kurtosis metric calculations, and delta of the second derivative (DSD) metric calculations from pre-processor 312. The down metric is the difference between a first (e.g., fiducial) sample of a fiducial-defined portion of the PPG signal and a minimum sample of the fiducial-defined portion of the PPG signal. The DSD metric is the delta (difference) between fiducial points in consecutive fiducial-defined portions of the second derivative of the PPG signal. Kurtosis measures the peakedness of a signal, such as the PPG signal, the first derivative of the PPG signal, or the second derivative of the PPG signal. In an exemplary embodiment, the kurtosis metric may be based on the first derivative of the PPG signal. The kurtosis of a signal may be calculated based on the following formulae:

$$D = \frac{1}{n}\sum_{i=1}^{n}(x'_i - \overline{x}')^2 \quad (14)$$

$$\text{Kurtosis} = \frac{1}{nD^2}\sum_{i=1}^{n}(x'_i - \overline{x}')^4 \quad (15)$$

where:
$x_i'$=ith sample of $1^{st}$ derivative;
$\vec{x}'$=mean of 1st derivative of fiducial-defined portion;
n=set of all samples in the fiducial-defined portion.

Processor 314 may utilize the received morphology metric values to calculate morphology metric signals and then to calculate respiration information signals and values from the morphology metric signals. Processor 314 may be coupled to post-processor 316 and may communicate respiration information to post-processor 316. Processor 314 may also provide other information to post-processor 316 such as the signal age related to the signal used to calculate the respiration information, and a time ratio representative of the useful portion of the respiration information signal. Pre-processor 312 may also provide information to post-processor 316 such as period variability, amplitude variability, and pulse rate information. Post-processor 316 may utilize the received information to calculate an output respiration information, as well as other information such as the age of the respiration information and status information relating to the respiration information output, e.g., whether a valid output respiration information value is currently available. Post-processor 316 may provide the output information to output 318.

Output 318 may be any suitable output device such as one or more medical devices (e.g., a medical monitor that displays various physiological parameters, a medical alarm, or any other suitable medical device that either displays physiological parameters or uses the output of post-processor 316 as an input), one or more display devices (e.g., monitor, PDA, mobile phone, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

In some embodiments, all or some of pre-processor 312, processor 314, and/or post-processor 316 may be referred to collectively as processing equipment. For example, processing equipment may be configured to amplify, filter, sample and digitize an input signal 310 and calculate physiological information from the signal.

Pre-processor 312, processor 314, and post-processor 316 may be coupled to one or more memory devices (not shown) or incorporate one or more memory devices such as any suitable volatile memory device (e.g., RAM, registers, etc.), non-volatile memory device (e.g., ROM, EPROM, magnetic storage device, optical storage device, flash memory, etc.), or both. The memory may be used by pre-processor 312, processor 314, and post-processor 316 to, for example, store data relating to input PPG signals, morphology metrics, respiration information, or other information corresponding to physiological monitoring.

It will be understood that system 300 may be incorporated into system 10 (FIGS. 1 and 2) in which, for example, input signal 310 may be generated by sensor unit 12 (FIGS. 1 and 2) and monitor 14 (FIGS. 1 and 2). Pre-processor 312, processor 314, and post-processor 316 may each be located in one of monitor 14 or display monitor 26 (or other devices), and may be split among multiple devices such as monitor 14 or display monitor 26. In some embodiments, portions of system 300 may be configured to be portable. For example, all or part of system 300 may be embedded in a small, compact object carried with or attached to the patient (e.g., a watch, other piece of jewelry, or a smart phone). In some embodiments, a wireless transceiver (not shown) may also be included in system 300 to enable wireless communication with other components of system 10 (FIGS. 1 and 2). As such, system 10 (FIGS. 1 and 2) may be part of a fully portable and continuous patient monitoring solution. In some embodiments, a wireless transceiver (not shown) may also be included in system 300 to enable wireless communication with other components of system 10. For example, communications between one or more of pre-processor 312, processor 314, and post-processor 316 may be over BLUETOOTH, 802.11, WiFi, WiMax, cable, satellite, Infrared, or any other suitable transmission scheme. In some embodiments, a wireless transmission scheme may be used between any communicating components of system 300.

Figure 4:
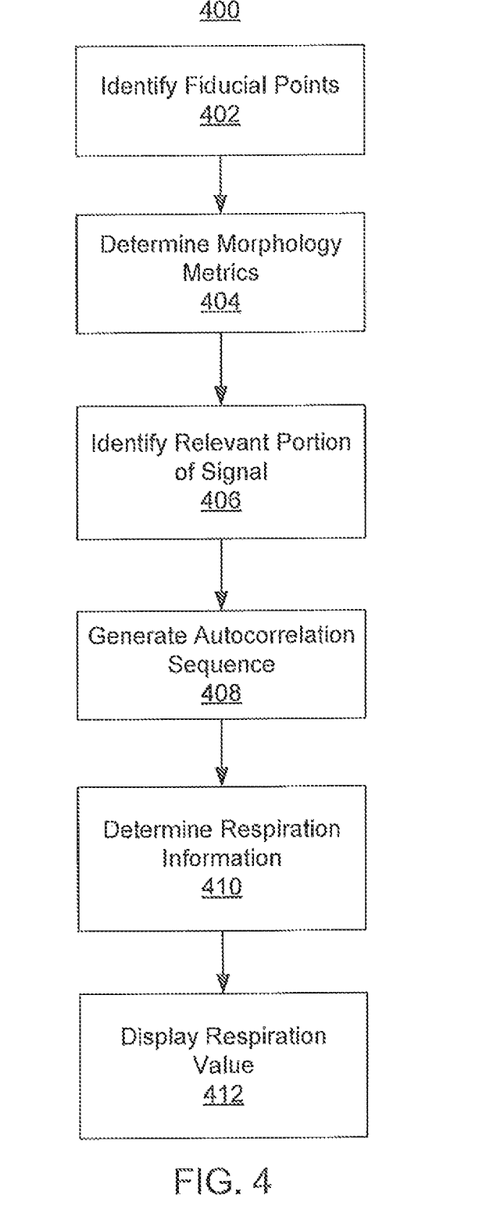
FIG. 4 is a flow diagram showing illustrative steps for determining respiration information from a photoplethysmograph signal in accordance with some embodiments of the present disclosure.

FIG. 4 is a flow diagram showing illustrative steps for determining a physiological parameter such as respiration information from a physiological signal such as a PPG signal in accordance with some embodiments of the present disclosure. Although an exemplary embodiment is described herein, it will be understood that each of steps 400 may be performed by pre-processor 312, processor 314, post-processor 316, or any combination thereof. It will also be understood that steps 400 may be performed in alternative sequence or in parallel, that steps may be omitted, and that additional steps may be added or inserted.

At step 402 pre-processor 312 may identify fiducial points for successive pulse waves of a PPG signal. Fiducial points may be identified in any suitable manner, for example based on peaks, troughs, slope values (e.g., the maximum slope of the PPG signal), and/or predetermined offsets. An example of determining fiducial points for a PPG signal is described in more detail in co-pending, commonly assigned U.S. patent application Ser. No. 13/243,907, filed Sep. 23, 2011 and entitled "SYSTEMS AND METHODS FOR DETERMINING RESPIRATION INFORMATION FROM A PHOTOPLETHYSMOGRAPH," which is incorporated by reference herein in its entirety. The fiducial points may define a series of fiducial defined portions that may be used as a reference for subsequent calculations, e.g., of morphology metric signals.

At step 404 pre-processor 312 may generate morphology metrics from the PPG signal. Morphology metric may be calculated from the PPG signal in any suitable manner. In one embodiment, a plurality of morphology metrics may be generated from the PPG signal. Example morphology metrics that may be relevant to determining a physiological parameter such as respiration information from a PPG signal may include a down metric, a kurtosis metric, a delta of DSD metric, an up metric, a skew metric, a b/a ratio metric, a c/a ratio metric, a i_b metric, a peak amplitude metric, a center of gravity metric, and an area metric. In an exemplary embodiment, morphology metric signals may be generated for the down metric, kurtosis metric, and DSD metric. For each morphology metric a sequence of morphology metric values, each corresponding to a fiducial defined region, may be calculated. The sequences of morphology metric values may be communicated to processor 314 to be attenuated, interpolated, and filtered to generate the morphology metric signals. Generating morphology metric signals from a PPG signal is described in more detail in co-pending, commonly assigned U.S. patent application Ser. No. 13/243,853, filed Sep. 23, 2011 and entitled "SYSTEMS AND METHODS FOR DETERMINING RESPIRATION INFORMATION FROM A PHOTOPLETHYSMOGRAPH," which is incorporated by reference herein in its entirety.

At step 406, pre-processor 312 may determine a usable portion of the PPG signal. Portions of the received signal may include samples with values that are unlikely to reflect actual values as a result of inaccurate measurement, user error, or other factors. Input signal 310 may be analyzed to identify divergences in the signal baseline, motion artifacts, divergences in pulse period, and any other signal features that may indicate inaccurate measurement, user error, or other factors. Based on this analysis, pre-processor 312 may identify portions of the input signal 310 to be ignored by processor 314 in calculating values such as respiration information. In one embodiment, Only those portions of the calculated morphology metric values that correspond to the usable portion of the input signal may be provided to processor 314.

At step 408, processor 314 may generate an autocorrelation sequence from the morphology metric signal. Although an autocorrelation sequence may be generated in any suitable manner, in one embodiment an autocorrelation sequence may be generated for each morphology metric signal and the autocorrelation sequences may be combined into a single autocorrelation sequence based on weighting factors. Generating the autocorrelation sequence from the morphology metric signals is described in more detail in co-pending, commonly assigned U.S. patent application Ser. No. 13/243,951, filed Sep. 23, 2011 and entitled "SYSTEMS AND METHODS FOR DETERMINING RESPIRATION INFORMATION FROM A PHOTOPLETHYSMOGRAPH," which is incorporated by reference herein in its entirety.

At step 410, processor 314 may determine respiration information based on the autocorrelation sequence. Respiration information may be determined from the autocorrelation sequence in any suitable manner. In one exemplary embodiment, a continuous wavelet transform may be used to determine respiration information such as respiration rate from the autocorrelation sequence, as is described in more detail in in co-pending, commonly assigned U.S. patent application Ser. No. 13/243,892, filed Sep. 23, 2011 and entitled "SYSTEMS AND METHODS FOR DETERMINING RESPIRATION INFORMATION FROM A PHOTOPLETHYSMOGRAPH," which is incorporated by reference herein in its entirety. In another exemplary embodiment, respiration information may be determined directly from the autocorrelation sequence, e.g., by comparing the peaks of the autocorrelation sequence to a threshold value or by identifying a maximum peak of the autocorrelation sequence within a window of interest. Determining respiration information directly from the autocorrelation sequence is described in more detail in co-pending, commonly assigned U.S. patent application Ser. No. 13/243,785, filed Sep. 23, 2011 and entitled "SYSTEMS AND METHODS FOR DETERMINING RESPIRATION INFORMATION FROM A PHOTOPLETHYSMOGRAPH," which is incorporated by reference herein in its entirety. As is described in more detail herein, the determination of respiration information may be modified based on a historical distribution of respiration values. The output respiration value may be communicated to post-processor 316.

At step 412, post-processor 316 may determine a display respiration value to be displayed, e.g., at the patient monitoring system. The display respiration value may be determined in any suitable manner. For example, the display respiration value may be based on the currently received respiration value. In another exemplary embodiment, the display respiration value may be based on the received respiration value as well as previously received respiration values. In an exemplary embodiment, post-processor 316 may calculate the display respiration value from the respiration value for the current analysis window and respiration values for one or more previous analysis windows, e.g., the five previous analysis windows.

Figure 5:
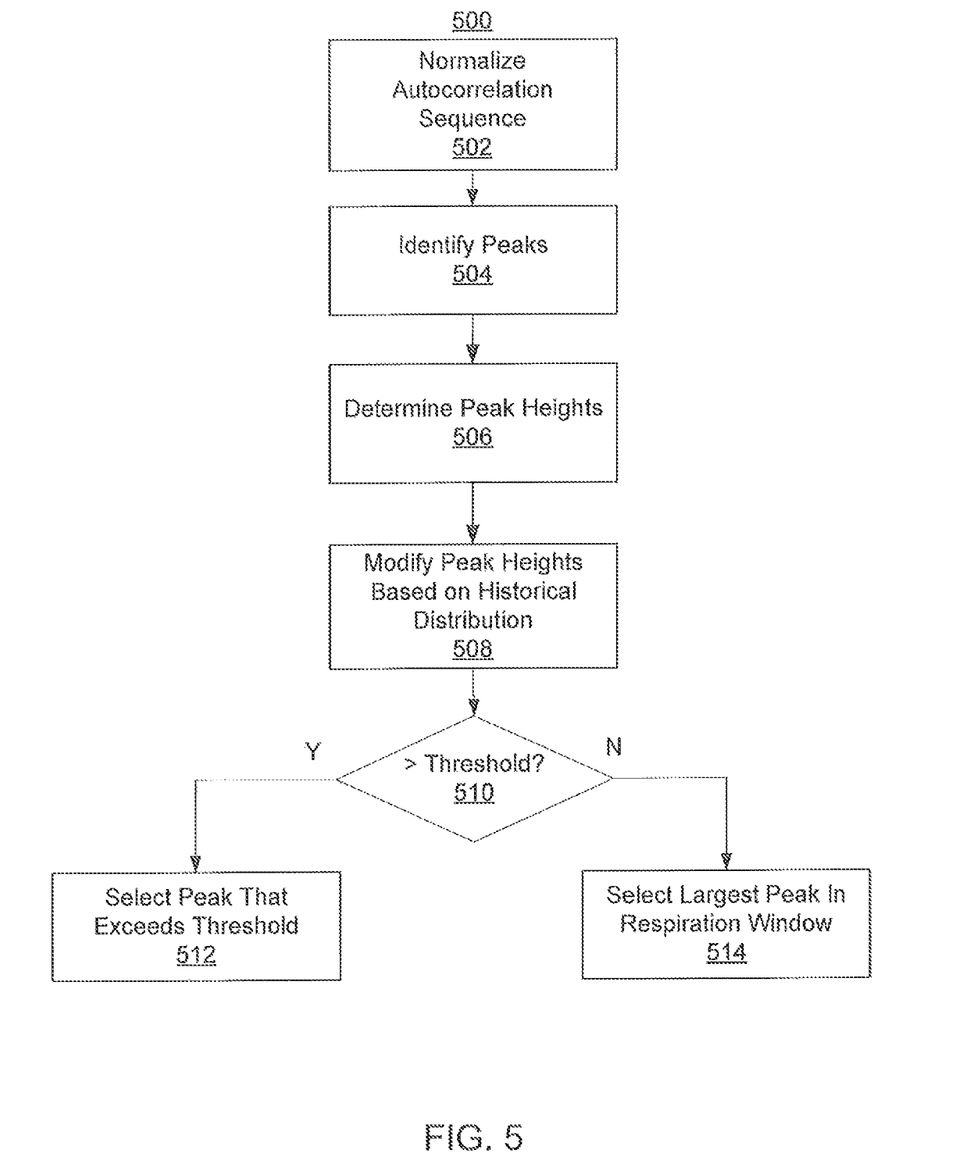
FIG. 5 is a flow diagram showing illustrative steps for selecting a modified autocorrelation peak based on a historical distribution in accordance with some embodiments of the present disclosure.

FIG. 5 is a flow diagram showing illustrative steps for selecting a modified autocorrelation peak based on a historical distribution in accordance with some embodiments of the present disclosure. Processor 314 may perform steps 500 to determine respiration information from the autocorrelation sequence, e.g., as an exemplary embodiment of determining respiration information in step 410 of FIG. 4. Although an exemplary embodiment is described herein, it will be understood that each of steps 500 may be performed by pre-processor 312, processor 314, post-processor 316, or any combination thereof. It will also be understood that steps 500 may be performed in alternative sequence or in parallel, that steps may be omitted, that additional steps may be added or inserted, and that the steps described herein may be modified for other methods of determining a physiological parameter such as respiration information, e.g., using a continuous wavelet transform.

At step 502, processor 314 may normalize the autocorrelation sequence. Although the autocorrelation sequence may be normalized in any suitable manner, in an exemplary embodiment the autocorrelation sequence may be normalized based on the maximum value of the autocorrelation sequence, e.g., by dividing each value in the autocorrelation sequence by the maximum value of the autocorrelation sequence, i.e., where the underlying morphology metric signal fully overlaps with itself. At step 504, processor 314 may identify each peak of the autocorrelation sequence. Although any suitable peaks may be identified for additional analysis, in an exemplary embodiment each local maxima may be identified to potentially determine respiration information. At step 506, the normalized peak height of each local maxima may be determined.

At step 508, processor 314 may modify each of the peak heights based on a historical distribution of data. In an exemplary embodiment, each peak of the autocorrelation sequence may correspond to a potential respiration value, e.g., in breaths per minute. However, in some instances the autocorrelation sequence may have peaks that correspond to periodic phenomena other than respiration, such as vasomotion or certain arrhythmias. If these peaks are selected the resulting respiration value may not be accurate and may instead reflect the other periodic phenomena.

Figure 6:
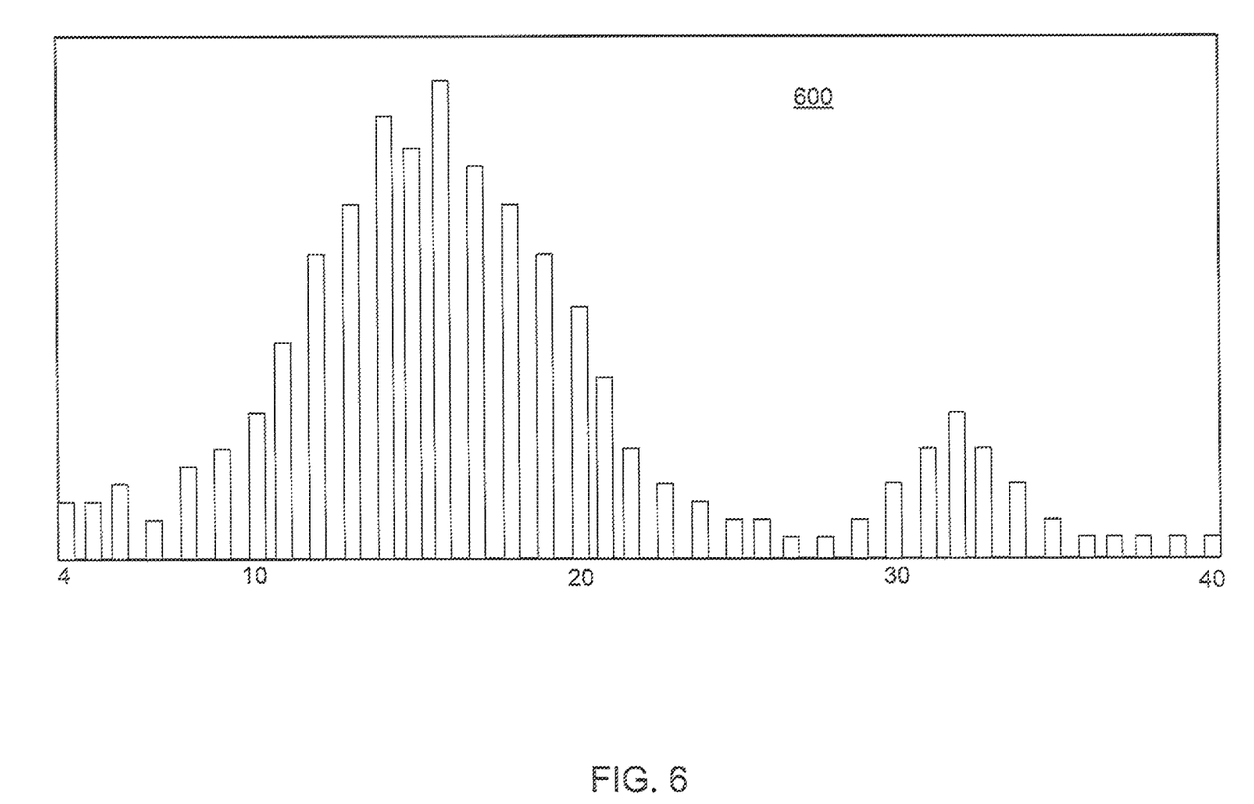
FIG. 6 shows an illustrative historical distribution of respiration values in accordance with some embodiments of the present disclosure.

Respiration generally changes slowly, and when respiration changes, tends to stay near a respiration rate for a period of time. In an exemplary embodiment, each peak of the autocorrelation sequence may be modified based on a historical distribution of respiration values. Referring to FIG. 6, an exemplary historical distribution 600 of respiration values is depicted. The abscissa of historical distribution 600 may be in units of breaths per minute, while the ordinate of historical distribution 600 may represent a relative historical weighting of the respiration values. An exemplary relevant range of respiration values may be from 4-40 breaths per minute. The historical distribution may be split into any appropriate resolution for updating, e.g., a resolution of 1 breath per minute. Although the relative historical weighting may be determined in any suitable manner, in an exemplary embodiment, more recent respiration values may receive a greater relative weight. For example, a weighting factor may be applied over time such that the historical distribution for all respiration values decreases over time, and such that recently updated respiration values are given additional weight.

Referring again to FIG. 5, at step 508 processor 314 may modify each of the peak heights of the autocorrelation sequence based on the historical distribution of data. Although the peak heights may be modified in any suitable manner, in an exemplary embodiment each peak height may be modified based on the fraction of the total historical distribution within a predetermined percentage of the respiration value corresponding the autocorrelation peak. Each peak height may be modified according to the following:

$$P_M = P_A + m^*(d_A - \overline{d}) \quad (14)$$

where:
$P_M$=modified peak height;
$P_A$=peak height;
m=weighting factor;
$d_A$=fraction of the distribution within x % of the peak; and
$\overline{d}$=mean fraction of the distribution for all peaks.

An exemplary value for m may be 0.5, while an exemplary percentage x % may be 20%. These values may be static or may be dynamic, e.g., based on factors such as a confidence value for the autocorrelation sequence or characteristics of the historical distribution. Once each peak has been modified as described above, the modified autocorrelation peak that corresponds to the respiration value may be determined in any suitable manner. An exemplary embodiment is described below with respect to steps 510-514.

At step 510, processor 314 may determine whether any modified peak value exceeds a threshold. If any modified peak value exceeds the threshold, processing may continue to step 512. At step 512, processor 314 may select from the modified peaks that exceed the threshold in any suitable manner. In an exemplary embodiment, processor 314 may select the first modified peak that exceeds the threshold, e.g., the peak corresponding the highest respiration value. If none of the modified peaks exceed the threshold, processing may continue to step 514. At step 514, processor 314 may select the largest modified peak within a respiration window of interest such as 4-40 breaths per minute. Once the modified peak has been selected as described herein, processing may continue, e.g., to determine a respiration value based on the modified peak.

Although the historical distribution may be updated in any suitable manner, in an exemplary embodiment all historical distributions that do not correspond to the selected respiration value may be decreased according to a weighting factor while the selected respiration value may be increased. In one embodiment the historical distribution value corresponding to the selected respiration value may be increased as follows:

$$D_N = D_P + w \quad (15)$$

where:
$D_N$=new historical distribution;

$D_p$=previous historical distribution; and
w=weighting factor.

In an exemplary embodiment, each of the remaining historical distribution values may be decreased as follows:

$$D_N=(1-w)*D_p \quad (16)$$

where:
$D_N$=new historical distribution;
$D_p$=previous historical distribution; and
w=weighting factor.

Although the weighting factor may be any suitable value, in an exemplary embodiment the weighting factor may be 0.01. This factor may be a fixed value or may be dynamically determined, e.g., based on characteristics of the historical distribution.

In some instances modifying an autocorrelation peak based on the historical distribution may yield an ambiguous result, e.g., multiple modified autocorrelation peaks may appear to correspond to possible respiration rates. In some embodiments it may be desirable to bypass the modifying steps based on the presence of an ambiguous result. For example, the unmodified autocorrelation sequence may have a single strong peak that predicts the respiration value with a high level of confidence. If a patient's respiration has changed or if the historical data is ambiguous, the historical distribution may result in an incorrect respiration value that may be reinforced over time. In some embodiments one or more factors such as the distribution of the historical data or a confidence level of the unmodified autocorrelation sequence may be analyzed to determine whether to bypass the modifying steps. Although these factors may be analyzed in any suitable manner, in an exemplary embodiment this analysis may be implemented using fuzzy logic. For example, each of the distribution of the historical data and the confidence of the unmodified autocorrelation sequence may be split into a number of possible classifications, and a series of rules for posting the data or changing the weighting of the current value may be created based on the classifications. For example, if the current unmodified autocorrelation sequence has a high level of confidence, and the historical distribution is likely to yield an ambiguous result, the unmodified autocorrelation sequence may be used to directly calculate the respiration value. It will be understood that different or additional inputs may be used to implement the fuzzy logic.

In other embodiments it may be desirable to adjust the relative weighting used to determine the respiration value. For example, there may be a bimodality or multimodality in the historical data, e.g., wherein an autocorrelation peak may correspond to more than one rate based on the historical distribution. In one embodiment, the weighting of the historical distribution in calculating the modified peak values may be reduced, e.g., based on a high level of confidence in the determination of the respiration value based on unmodified peak values. In another embodiment, the modified peak value may be assigned a lower weight relative to the current displayed value in determining the value to be displayed on the patient monitoring unit by post-processor 316. Although these factors may be analyzed in any suitable manner, in an exemplary embodiment this analysis may be implemented using fuzzy logic. For example, each of the distribution of the historical data and the confidence of the unmodified autocorrelation sequence may be split into a number of possible classifications, and a series of rules for posting the data or changing the weighting of the current value may be created based on the classifications. For example, if the current unmodified autocorrelation sequence does not have a high level of confidence, and the historical distribution is exhibiting bimodality, an indication may be provided to post-processor 316 to decrease the weighting of the current respiration value in calculating the display value, i.e., to weight the display value more heavily towards previous display values. It will be understood that different or additional inputs may be used to implement the fuzzy logic.

The foregoing is merely illustrative of the principles of this disclosure and various modifications may be made by those skilled in the art without departing from the scope of this disclosure. The above described embodiments are presented for purposes of illustration and not of limitation. The present disclosure also can take many forms other than those explicitly described herein. Accordingly, it is emphasized that this disclosure is not limited to the explicitly disclosed methods, systems, and apparatuses, but is intended to include variations to and modifications thereof, which are within the spirit of the following claims.

What is claimed is:

1. A method for determining a respiration rate from a photoplethysmograph (PPG) signal, the method comprising:
    generating a plurality of morphology metric signals based on the PPG signal;
    generating an autocorrelation sequence based on the plurality of morphology metric signals;
    determining, using processing equipment, a plurality of peak values based on the autocorrelation sequence;
    accessing, using the processing equipment, a historical distribution of the respiration rate; and
    for each of the plurality of peak values:
        associating, using the processing equipment, the peak value with a first portion of the historical distribution of the respiration rate; and
        adjusting, using the processing equipment, the peak value based on the first portion of the historical distribution of the respiration rate;
    and
    calculating, using processing equipment, an updated value of the respiration rate based on the adjusted plurality of peak values.

2. The method of claim 1, wherein, for each of the plurality of peak values, adjusting the peak value comprises weighting the peak value based on a total distribution of the respiration rate within the first portion of the historical distribution.

3. The method of claim 1, wherein calculating the updated value of the respiration rate comprises:
    comparing the adjusted plurality of peak values to a threshold;
    selecting the first adjusted peak value that exceeds the threshold; and
    calculating the updated value of the respiration rate based on the selected adjusted peak value.

4. The method of claim 1, wherein calculating the updated value of the respiration rate comprises:
    selecting the maximum modified peak value within a window of interest; and
    calculating the updated value of the respiration rate based on the selected adjusted peak value.

5. The method of claim 1 further comprising updating the historical distribution based on the updated value of the respiration rate.

6. The method of claim 5 wherein updating the historical distribution comprises:
    identifying a portion of the historical distribution associated with the respiration rate;

increasing one or more historical distribution values associated with the identified portion; and decreasing one or more historical distribution values that are not associated with the identified portion.

7. The method of claim 1, further comprising generating, using processing equipment, a confidence value based on the plurality of peak values, wherein the updated value of the respiration rate is calculated based on the confidence value and the adjusted plurality of peak values.

8. A patient monitoring system for monitoring a respiration rate, the system comprising:
an interface configured to receive a photoplethysmograph (PPG) signal; and
a processor configured to:
generate a plurality of morphology metric signals based on the PPG signal;
generate an autocorrelation sequence based on the plurality of morphology metric signals;
determine a plurality of peak values based on the autocorrelation sequence;
access a historical distribution of the respiration rate; and
for each of the plurality of peak values:
associate the peak value with a first portion of the historical distribution of the respiration rate; and
adjust the peak value based on the first portion of the historical distribution of the respiration rate; and
calculate an updated value of the respiration rate based on the adjusted plurality of peak values.

9. The patient monitoring system of claim 8, wherein the processor is further configured to, for each of the plurality of peak values, adjust the peak value based on a total distribution of the respiration rate within the first portion of the historical distribution.

10. The patient monitoring system of claim 8, wherein the processor is further configured to:
compare the adjusted plurality of peak values to a threshold;
select the first adjusted peak value that exceeds the threshold; and
calculate the updated value of the respiration rate based on the selected adjusted peak value.

11. The patient monitoring system of claim 8, wherein the processor is further configured to:
select the maximum adjusted peak value within a window of interest; and
calculate the updated value of the respiration rate based on the selected adjusted peak value.

12. The patient monitoring system of claim 8 wherein the processor is further configured to update the historical distribution based on the updated value of the respiration rate.

13. The patient monitoring system of claim 12 wherein the processor is configured to update the historical distribution by:
identifying a portion of the historical distribution associated with the respiration rate;
increasing one or more historical distribution values associated with the identified portion; and
decreasing one or more historical distribution values that are not associated with the identified portion.

14. The patient monitoring system of claim 8, wherein the processor is further configured to generate a confidence value based on the plurality of peak values, wherein the updated value of the respiration rate is calculated based on the confidence value and the adjusted plurality of peak values.

* * * * *